(12) United States Patent
Ahn

(10) Patent No.: US 7,724,368 B2
(45) Date of Patent: *May 25, 2010

(54) CONDENSATION PARTICLE COUNTER

(76) Inventor: Kang Ho Ahn, 5-804, Sunkyung Apartment, 506, Daechi-dong, Gangnam-ku, Seoul 135-836 (KR)

(*) Notice: Subject to any disclaimer, the term of this patent is extended or adjusted under 35 U.S.C. 154(b) by 0 days.

This patent is subject to a terminal disclaimer.

(21) Appl. No.: 12/166,202

(22) Filed: Jul. 1, 2008

(65) Prior Publication Data

US 2009/0009749 A1 Jan. 8, 2009

(30) Foreign Application Priority Data

Jul. 5, 2007 (KR) .................. 10-2007-0067518

(51) Int. Cl.
*G01N 15/02* (2006.01)
(52) U.S. Cl. .................. 356/336; 356/337; 377/10
(58) Field of Classification Search .................. 356/37, 356/335–343; 377/10–11
See application file for complete search history.

(56) References Cited

U.S. PATENT DOCUMENTS

| | | | | |
|---|---|---|---|---|
| 5,026,155 A | * | 6/1991 | Ockovic et al. | 356/37 |
| 5,118,959 A | * | 6/1992 | Caldow et al. | 250/573 |
| 2003/0202169 A1 | * | 10/2003 | Liu | 356/37 |
| 2004/0012772 A1 | * | 1/2004 | Ahn et al. | 356/37 |
| 2005/0248750 A1 | * | 11/2005 | Flagan et al. | 356/37 |
| 2008/0186489 A1 | * | 8/2008 | Ahn | 356/337 |
| 2009/0009748 A1 | * | 1/2009 | Ahn | 356/37 |

* cited by examiner

*Primary Examiner*—Hoa Q Pham
(74) *Attorney, Agent, or Firm*—Lowe Hauptman Ham & Berner LLP

(57) ABSTRACT

A condensation particle counter is capable of efficiently measuring the number and size of fine particles. The condensation particle counter includes a saturator, a condenser and an optical particle counters. The saturator is designed to generate a saturated gas by saturating a gas in which fine particles are suspended with working fluid. The condenser is connected to a downstream side of the saturator to condense the saturated gas so that liquid droplets can grow around the fine particles. The optical particle counter is connected to downstream sides of the condenser to optically detect the liquid droplets supplied from the condensers. The condenser has a condenser tube for interconnecting the saturator and the optical particle counter. The present condensation particle counter can use water as working fluid and also can optically measure fine particles in an easy and accurate manner by forming or installing an inner surface of a condenser tube with a hydrophilic tube.

5 Claims, 5 Drawing Sheets

CONDENSATION PARTICLE COUNTER

RELATED APPLICATION

The present application is based on, and claims priority from, Korea Application Number 10-2007-0067518, filed Jul. 5, 2007, the disclosure of which is hereby incorporated by reference herein in its entirety.

FIELD OF THE INVENTION

The present invention relates to a condensation particle counter. Especially, the present invention relates to a condensation particle counter using water as a working fluid for efficiently measuring the number and size of fine particles.

BACKGROUND OF THE INVENTION

A condensation particle counter comprises a saturator, a condenser and an optical particle counter (OPC) and is widely used in measuring the number and size of fine particles. The saturator of the condensation particle counter contains working fluid to saturate an aerosol, i.e., a particle-suspended gas. Examples of the working fluid include alcohol-based fluid such as alcohol, butanol, isopropyl alcohol or the like and organic compound fluid such as ethylene glycol or the like.

The saturator is heated by a heater and kept at a temperature higher than an ambient temperature, as a result of which the working fluid contained in the saturator is evaporated. If the particle-suspended gas is introduced into the saturator, it is saturated by the working fluid and turned to a saturated gas which in turn is supplied to the condenser from the saturator. In case of using alcohol as the working fluid, the saturator is kept at a temperature of 35° C. and the condenser is kept at a temperature of 10° C. As the temperature of the condenser drops, the saturated gas is turned to a supersaturated gas. Condensation of the saturated gas occurs in such a fashion that liquid droplets grow bigger around fine particles as their nuclei. The liquid droplets thus grown are supplied to the optical particle counter. If the saturated gas is diffused faster than the heat transfer speed in the condenser, the saturated gas is not condensed around the fine particles but condensed only on the wall surface of the condenser. The optical particle counter is designed to count the number and size of the fine particles by detecting the liquid droplets.

There are provided many advantages if water is used as the working fluid of the condensation particle counter. This is because water is not harmful to the human body and does not generate any odor or pollutant. In case water is used as the working fluid in the conventional condensation particle counter, however, the water vapor is condensed only on the wall surface of the condenser that remains at a low temperature and there occurs no condensation that uses fine particles as nuclei. Therefore, the fine particles are discharged as they are. This poses a problem in that the fine particles cannot be detected by means of the optical particle counter.

For the reasons mentioned above, the conventional condensation particle counter makes use of an organic compound as the working fluid. The organic compound is detrimental to the human body and gives off a strong smell. In addition, the organic compound is highly difficult to handle because it is flammable. Particularly, if an alcohol-based organic material is used as the working fluid of the condensation particle counter in a semiconductor manufacturing process, the organic material acts as a pollutant and therefore becomes a cause of defect. Inasmuch as the organic compound tends to absorb moisture contained in a gas, the condensation particle counter suffers from degradation in performance if the organic compound is used for a long period of time. Thus, there is a need to periodically replace the organic compound, which task is onerous.

The conventional condensation particle counter has a fixed aerosol measuring capacity. Therefore, several condensation particle counters have to be used in combination in order to measure a large quantity of aerosol in one place, which is cumbersome and inconvenient. Furthermore, in case of using several condensation particle counters at one time, it is very difficult to uniformly control the temperature of the saturator and the condenser of the individual condensation particle counters. If a great deviation exists in the temperature of the saturator and the condenser, the data obtained by measuring the fine particles become less reliable.

SUMMARY OF THE INVENTION

In view of the above-noted and other problems inherent in the prior art, it is an object of the present invention to provide a condensation particle counter that uses water as working fluid by forming an inner surface of a condenser tube with a hydrophilic layer.

With these objects in view, the present invention provides a condensation particle counter, comprising:

a saturator generating a saturated gas by saturating a gas in which fine particles are suspended with working fluid;

a condenser connected to a downstream side of the saturator and condensing the saturated gas so that liquid droplets grow around the fine particles; and an optical particle counter connected to downstream sides of the condenser and optically detecting the liquid droplets supplied from the condenser;

wherein the condenser has a condenser tube interconnecting the saturator and the optical particle counter, the condenser tube provided with a hydrophilic tube installed inside surface of the condenser tube. The hydrophilic tube is made of a titanium oxide ($TiO_2$). The working fluid includes water.

BRIEF DESCRIPTION OF THE DRAWINGS

The above and other objects and features of the present invention will become apparent from the following description of a preferred embodiment, given in conjunction with the accompanying drawings, in which.

DETAILED DESCRIPTION OF THE PREFERRED EMBODIMENTS

A preferred embodiment of a condensation particle counter in accordance with the present invention will now be described in detail with reference to the accompanying drawings.

Figure 1:
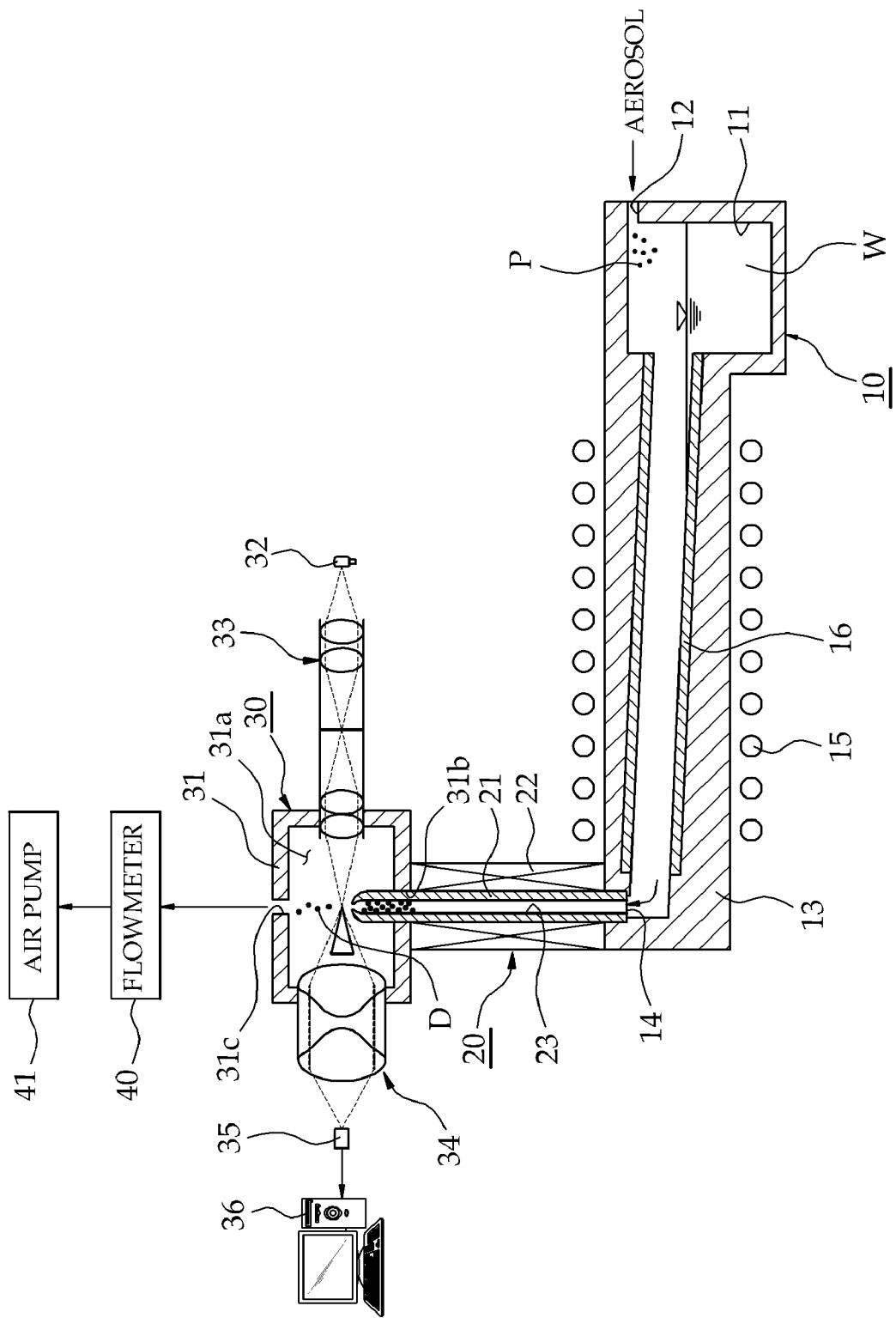
FIG. 1 is a section view showing a configuration of a condensation particle counter in accordance with the present invention.

Referring first to FIG. 1, a condensation particle counter of the present invention includes a saturator 10 for generating a saturated gas by allowing working fluid to saturate a gas in which fine particles P is suspended, a condenser 20 for condensing the saturated gas and an optical particle counter 30 for optically detecting the fine particles P to calculate the number and size of the fine particles P.

The saturator 10 is provided with a pool 11 that contains working fluid W. The pool 11 is connected to an inlet port 12 of the saturator 10 through which an aerosol, i.e., a gas in which fine particles P are suspended, is introduced. A saturator tube 13 for guiding the stream of the saturated gas is connected to one side of the pool 11. The saturator tube 13 has an outlet port 14 through which the saturated gas is discharged. The level of the working fluid W is kept lower than the inlet port 12 and the outlet port 14 so that the gas stream can be guided across the level surface of the working fluid W. A heater 15 is attached to the outside of the saturator 10. The heater 15 serves to heat and evaporate the working fluid W contained in the pool 11. Attached to an inner surface of the saturator tube 13 is an absorption member 16 that absorbs the working fluid W contained in the pool 11 to thereby accelerate evaporation of the working fluid W. Water, alcohol-based fluid or the like may be used as the working fluid W. Use of water is preferred.

Figure 2:
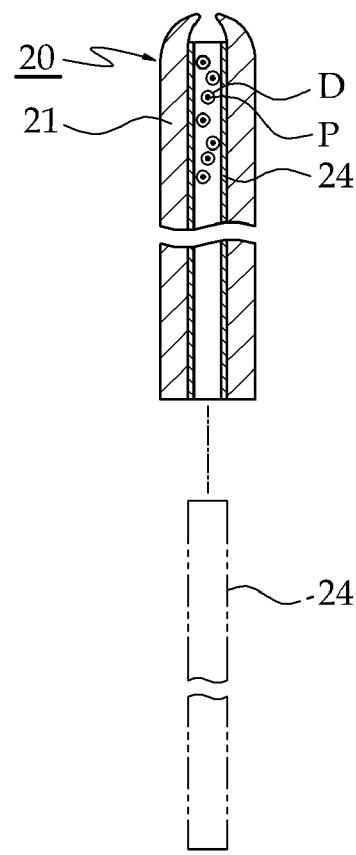
FIG. 2 is a sectional view illustrating a configuration of a condensation particle counter in which a hydrophilic tube is installed inside surface of the condensation tube according to the present invention.
Figure 3:
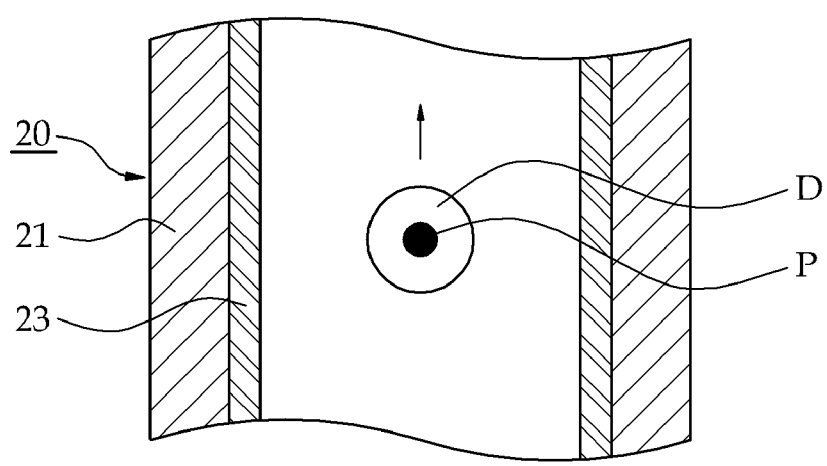
FIG. 3 is an enlarged view illustrating a state that a liquid droplet is formed around a fine particle as a nucleus within a condenser tube of the present condensation particle counter.

Referring to FIGS. 1 to 3, the condenser 20 is connected to the downstream side of the saturator 10. The condenser 20 serves to condense the saturated gas so that liquid droplets D can be formed around nuclei, i.e., the fine particles P supplied from the saturator 10. The condenser 20 includes a condenser tube 21 connected to the outlet port 14 of the saturator 10. Mounted to an outer surface of the condenser tube 21 is a thermoelectric cooler 22 that serves as a cooling means for reducing the temperature of the condenser tube 21. Alternatively, the cooling means may be formed of a cooling device that includes a cooling chamber surrounding the outer surface of the condenser tube 21 and a refrigerating cycle for reducing the temperature of the condenser tube 21 by supplying coolant into the cooling chamber.

A hydrophilic tube 25 that allows water to be used as the working fluid W is formed on an inner surface of the condenser tube 21. The hydrophilic tube 25 can be made of a titanium oxide ($TiO_2$) or a hydrophilic polymer. Alternatively, the hydrophilic tube 25 can be formed by coating a hydrophilic material, e.g., titanium oxide ($TiO_2$), on the inner surface of the condenser tube 21 or by using a plasma surface modification. With the plasma surface modification, a titanium oxide layer is formed on the inner surface of the condenser tube 21 by use of plasma generated in a well-known plasma surface modification apparatus.

Figure 4:
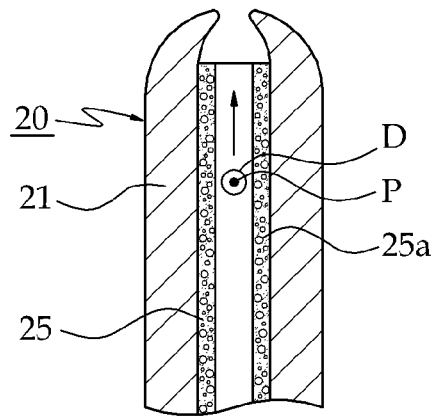
FIG. 4 is a sectional view illustrating a configuration of a condensation particle counter in which a porous tube is installed inside surface of the condensation tube according to one example of the hydrophilic tube.

Referring to the FIG. 4, the hydrophilic tube 25 is formed by a porous tube having a plurality of air hole 25a. The porous tube is made of the titanium oxide ($TiO_2$), the hydrophilic polymer, or Zeolite.

As can be seen in FIG. 1, the optical particle counter 30 is connected to the downstream side of the respective condenser 20. The optical particle counter 30 serves to calculate the number and size of the fine particles P by optically detecting the liquid droplets D supplied from the condenser tube 21. The optical particle counter 30 includes a housing 31, a light source 32, a first lens array 33, a second lens array 34, a photo detector 35 and a computer 36.

The housing 31 has an inlet port 31b, an outlet port 31c and a sensing volume 31a arranged between the inlet port 31b and outlet port 31c. The condenser tube 21 is connected to the inlet port 31b of the housing 31. The light source 32 is mounted to one side of the housing 31 and is designed to emit light which in turn is irradiated into the sensing volume 31a of the housing 31 through the first lens array 33. The light irradiated into the sensing volume 31a of the housing 31 is collected by means of the second lens array 34 attached to the other side of the housing 31. The light collected by the second lens array 34 is detected by means of the photo detector 35.

The photo detector 35 is designed to input optical signals to the computer 36. The computer 36 calculates the number and size of the fine particles P by processing the optical signals inputted from the photo detector 35 with a pre-stored program. The photo detector 35 is formed of an image sensor for acquiring positional data of the liquid droplets D, e.g., a charge coupled device (CCD) camera or a quadrature detector. The computer 36 may include a signal processor that calculates the number and size of the fine particles P by processing the optical signals inputted from the photo detector 35. A flowmeter 40 for measuring the flow rate of the gas and an air pump 41 for drawing the gas are serially connected to the outlet port 31c of the housing 31.

Description will now be made regarding an operation of the present condensation particle counter configured as above.

Referring again to FIGS. 1 and 2, water as the working fluid W is contained in the pool 11 of the saturator 10. If the temperature of the saturator 10 is increased to about 60° C. to 70° C. by the operation of the heater 15, the water is evaporated to generate water vapor. If the air pump 41 is operated to exert a (inhaling) vacuum force, the aerosol, i.e., the gas in which the fine particles P are suspended, is introduced into the pool 11 through the inlet port 12 of the saturator 10. The gas is saturated into a saturated gas by the water vapor and then discharged through the outlet port 14.

The condenser tube 21 of the condenser 20 connected to the outlet port 14 of the saturator 10 is kept at a temperature lower than the temperature of the saturator 10 by means of the thermoelectric cooler 22. The condenser tube 21 is maintained at a temperature of about 20° C., which is about 10° C. higher than the temperature available in the conventional condensation particle counter that uses alcohol-based fluid as the working fluid. Thus, the water vapor is condensed around the fine particles P suspended in the gas, thereby generating liquid droplets D, i.e., water droplets. At this time, the saturator 10 is kept at a temperature of about 60° C. to 70° C. and the condenser tube 21 is maintained at a temperature of about 20° C. This helps optimize the generation of the liquid droplets D while assuring increased energy efficiency.

The liquid droplets D generated on the inner surface of the condenser tube 21 are readily moved down along the surface of the hydrophilic inner surface under the gravity force. In a case that the inner surface of the condenser tube 21 is hydrophobic, the liquid droplets D would be unable to move down along but adhere to the inner surface of the condenser tube 21. The liquid droplets D adhering to the inner surface of the condenser tube 21 hinders heat transfer, consequently making uneven the temperature distribution within the condenser tube 21. Therefore, the degree of super saturation within the condenser tube 21 becomes very uneven, which obstructs growth of the liquid droplets D around the fine particles P as their nuclei.

Figure 5:
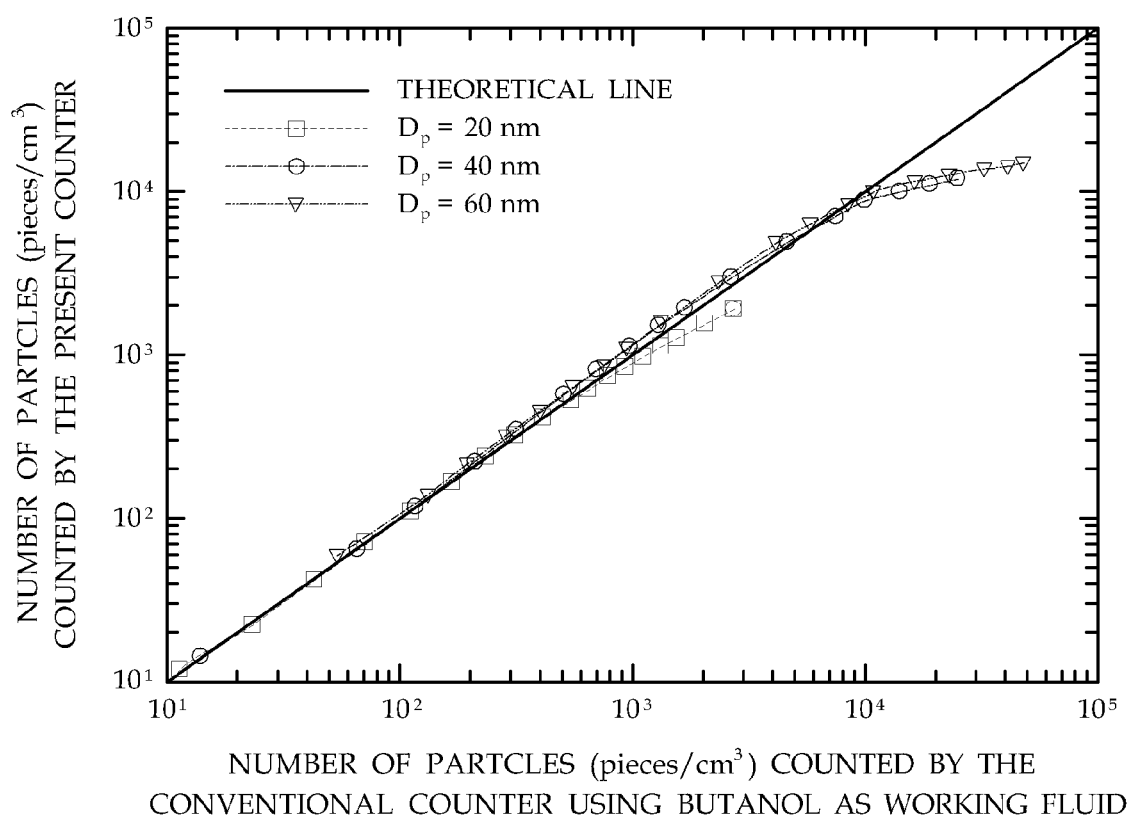
FIG. 5 is a graph plotting a performance test result of the present condensation particle counter against that of a conventional condensation particle counter which makes use of butanol as working fluid.

For the case that a hydrophilic tube 25 is installed inside surface of the condenser tube 21, the liquid droplets D are generated on the inner surface the hydrophilic tube 25 because the hydrophilic tube 25 is contact with the inside surface of the condenser tube 21. Therefore, the liquid droplets D are readily moved down along the surface of the hydrophilic tube 25 under the gravity force. Especially, for the case that a porous tube is installed inside surface of the condenser tube 21 as shown in FIG. 5, the liquid droplets D are generated on the inner surface the porous tube because the porous tube is contact with the inside surface of the condenser tube 21. The plurality of air hole 25a of the porous tube absorbs the liquid droplets D.

Referring again to FIGS. 1 and 3, the liquid droplets D is introduced into the sensing volume 31a of the optical particle counter 30 through the condenser tube 21 and then discharged to the outside of the housing 31 from the sensing volume 31a through the outlet port 31c. The light source 32 irradiates light into the sensing volume 31a via the first lens array 33. The light thus irradiated is scattered by the liquid droplets D flowing through the sensing volume 31a. The scattered light is sent to the photo detector 35 via the second lens array 34. Upon detecting the light, the photo detector 35 generates optical signals. The computer 36 calculates the number and size of the fine particles P by processing the optical signals inputted from the photo detector 35 with a pre-stored program. The number and size of the fine particles P thus calculated is displayed on a display device such as a monitor or the like. The fine particles P and the liquid droplets D discharged to the outside through the outlet port 31c of the housing 31 are removed by means of a filter.

Performance tests were conducted for the present condensation particle counter and the conventional condensation particle counter. FIG. 5 is a graph plotting a performance test result of the present condensation particle counter against that of the conventional condensation particle counter which makes use of butanol as working fluid. The present condensation particle counter differs from the conventional condensation particle counter in that a hydrophilic tube including a titanium oxide is formed on the inner surface of the condenser tube. Water was used as the working fluid in the present condensation particle counter, while butanol was used as the working fluid in the conventional condensation particle counter. It can be seen in FIG. 5 that the number of the fine particles measured by the present condensation particle counter is substantially equal to that measured by the conventional condensation particle counter until the concentration of the fine particles having particle diameters ($D_p$) of 20 nm, 40 nm and 60 nm reaches 10,000 pieces/cm$^3$. It can also be appreciated that the numbers of the fine particles measured by the present condensation particle counter and the conventional condensation particle counter nearly coincide with a theoretical line.

Figure 6:
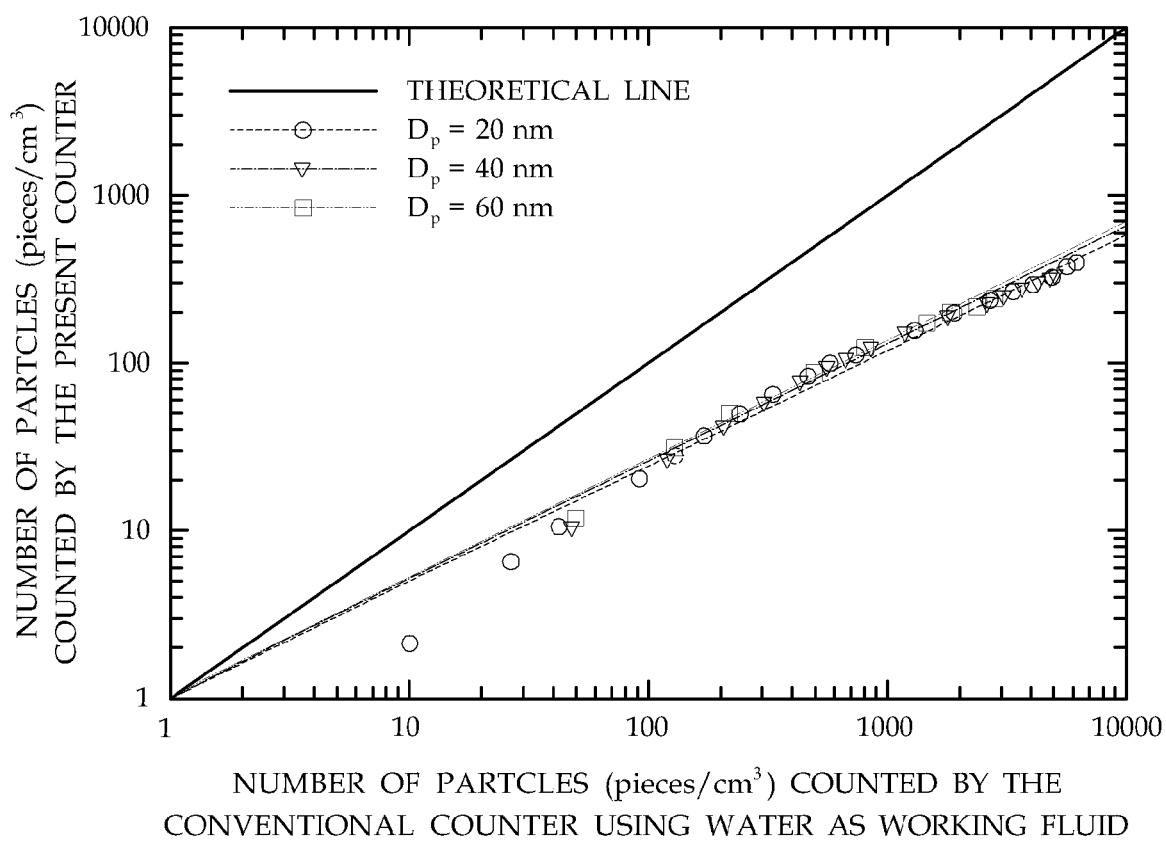
FIGS. 6 and 7 are graphs plotting performance test results of the present condensation particle counter against those of a conventional condensation particle counter which makes use of water as working fluid.
Figure 7:
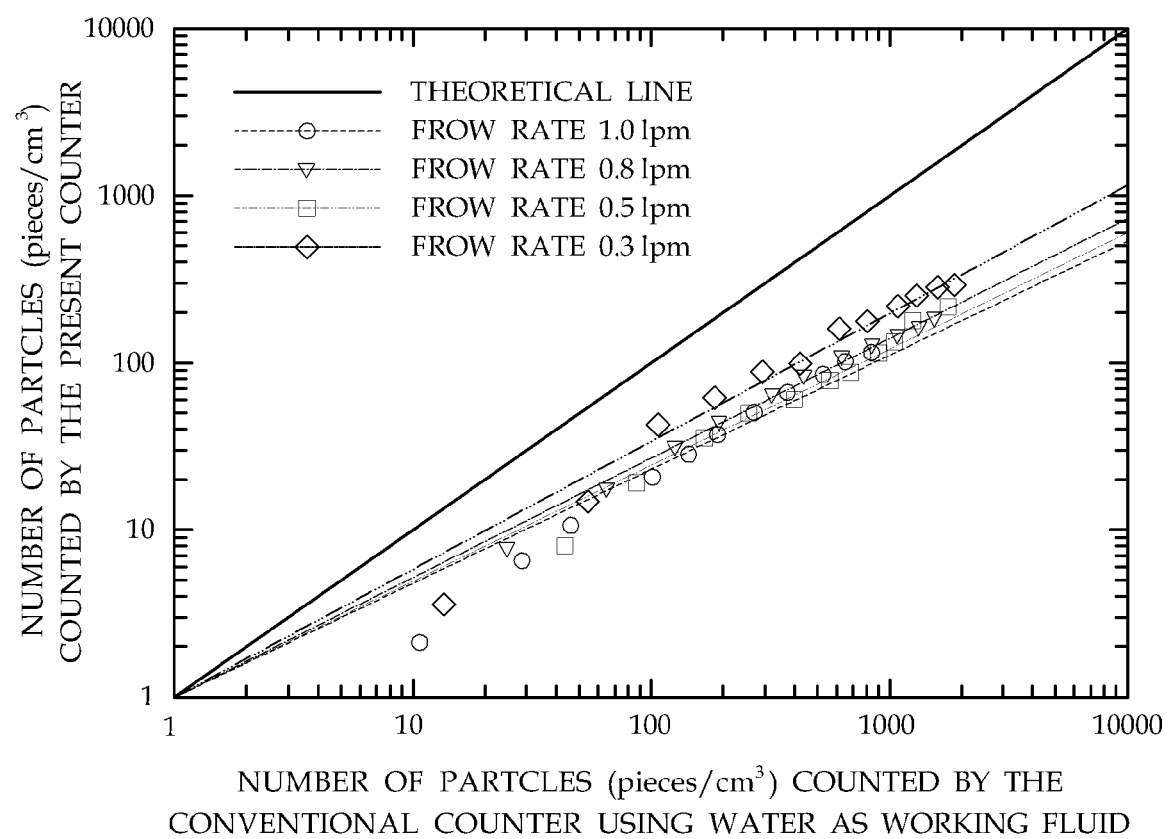

Performance tests were conducted for the present condensation particle counter and the conventional condensation particle counter, both of which make use of water as working fluid. FIGS. 6 and 7 are graphs plotting the performance test results of the present condensation particle counter against those of a conventional condensation particle counter. The graph shown in FIG. 6 illustrates the result of test for the fine particles having particle diameters ($D_p$) of 20 nm, 40 nm and 60 nm, which test was conducted at an aerosol flow rate of 1.01 pm (liter per minute). The graph shown in FIG. 7 illustrates the result of test conducted at different aerosol flow rates of 1.01 pm, 0.81 pm, 0.51 pm and 0.31 pm. It can be seen in FIGS. 6 and 7 that the particle counting efficiency achieved by the conventional condensation particle counter is as low as about 10% with respect to a theoretical line obtained by the present condensation particle counter.

As described hereinabove, the present condensation particle counter can use water as working fluid and also can optically measure fine particles in an easy and accurate manner by forming or installing an inner surface of a condenser tube with a hydrophilic tube.

The embodiment set forth hereinabove have been presented for the illustrative purpose only and, therefore, the present invention is not limited to the foregoing embodiment. It will be understood by those skilled in the art that various changes and modifications may be made without departing from the scope of the invention defined in the claims.

What is claimed is:

1. A condensation particle counter, comprising:
  a saturator generating a saturated gas by saturating a gas in which fine particles are suspended with working fluid;
  a condenser connected to a downstream side of the saturator and condensing the saturated gas so that liquid droplets grow around the fine particles; and
  an optical particle counter connected to downstream sides of the condenser and optically detecting the liquid droplets supplied from the condensers;
  wherein the condenser has a condenser tube interconnecting the saturator and the optical particle counter, the condenser tube provided with a hydrophilic tube installed on an inside surface of the condenser tube.

2. The condensation particle counter as recited in claim 1, wherein the hydrophilic tube is a porous tube having a plurality of air holes.

3. The condensation particle counter as recited in claim 2, wherein the hydrophilic tube includes selected one of titanium oxide, hydrophilic polymer and zeolite.

4. The condensation particle counter as recited in claim 1, wherein the working fluid comprises water.

5. The condensation particle counter as recited in claim 4, wherein the saturator is kept at a temperature of about 60° C. to 70° C. and the condenser tube is maintained at a temperature of about 20° C.

* * * * *